(12) United States Patent
Kim

(10) Patent No.: US 6,888,546 B1
(45) Date of Patent: May 3, 2005

(54) THREE-DIMENSIONAL IMAGE DISPLAY, DISPLAY METHOD, PROGRAM FOR DISPLAY

(76) Inventor: Han-Joon Kim, c/o KIM Orthodontic Clinic, 5-5, Funado-cho, Ashiya-shi, Hyogo, 659-0093 (JP)

( * ) Notice: Subject to any disclaimer, the term of this patent is extended or adjusted under 35 U.S.C. 154(b) by 261 days.

(21) Appl. No.: 10/019,011

(22) PCT Filed: Jun. 28, 2000

(86) PCT No.: PCT/JP00/04235

§ 371 (c)(1),
(2), (4) Date: Dec. 26, 2001

(87) PCT Pub. No.: WO01/03065

PCT Pub. Date: Jan. 11, 2001

(30) Foreign Application Priority Data

Jun. 30, 1999 (JP) .......................................... 11-185865
May 24, 2000 (JP) ...................................... 2000-153563

(51) Int. Cl.⁷ ............................................. G06T 17/00
(52) U.S. Cl. ...................... 345/424; 345/419; 345/427; 345/629; 600/407; 600/438
(58) Field of Search ............................... 345/424, 427, 345/419, 429, 629; 600/407, 438

(56) References Cited

FOREIGN PATENT DOCUMENTS

| JP | 08-131403 | * | 5/1996 |
| JP | 10-137231 |   | 5/1998 |
| WO | WO 01/03065 A1 | | 1/2000 |

* cited by examiner

Primary Examiner—Kimbinh T. Nguyen
(74) Attorney, Agent, or Firm—Rabin & Berdo, P.C.

(57) ABSTRACT

A three-dimensional image displayed by a conventional medical computer system is not displayed on the basis of anatomic landmarks, so that a plurality of images cannot be compared with one another and examined on the basis of the same reference surfaces and references. In this invention, a three-dimensional image is constructed and displayed on the basis of multi-tomographing image data. Anatomic landmarks in the displayed three-dimensional image are specified, and reference planes are created on the basis of the landmarks. When the reference planes are created, the three-dimensional image is displayed upon correcting the position thereof such that it becomes an image based on the reference planes. As a result, an image displayed in three dimensions is an image based on anatomic reference planes, so that it can be anatomically directed in three-dimensions. Therefore, it is possible to obtain an image having good reproducibility.

16 Claims, 11 Drawing Sheets

THREE-DIMENSIONAL IMAGE DISPLAY, DISPLAY METHOD, PROGRAM FOR DISPLAY

TECHNICAL FIELD

The present invention relates to a device for and a method of displaying a three-dimensional image, and a program for displaying a three-dimensional image in a medical computer system.

BACKGROUND

As an example of a medical field, description is made by taking orthodontics as an example.

In the orthodontics, medical treatment of malocclusion, for example, improvements of so-called projecting teeth, a mouth with a protruding lower lip, a teeth arrangement is provided. However, the treatment is not for merely regularly arranging teeth. For example, a teeth arrangement and occlusion of an anterior tooth portion are deeply related to aesthetic properties of a mouth and a complexion. The occlusion is constituted by a pair of maxillary dentition and mandibular dentition. In order to obtain good results of treatment by both the occlusion and the complexion, therefore, the position of teeth in a maxilla and a mandible, the deviation between the maxilla and the mandible, and the positional relationship of the mandible in a skull, and so forth must be sufficiently considered to provide treatment.

Cephalometrics films which have been introduced from about 1940 are frequently used as indispensable examination materials for obtaining a lot of information relating to teeth, a maxilla, a mandible and a skull in a clinical study of the orthodontics even at the present time.

Anatomical measuring points (landmarks) on bones are common among human beings, and are widely used in knowing the difference in a skeletal form between races and respective skeletal forms. In the orthodontics, the distance and the angle between the landmarks are calculated, and are used for classifying the patterns of the skeletal forms of patients and the positions of their teeth, and so forth, specifying problems, making various diagnoses such as treatment plans, and evaluating changes before and after treatment and changes by growth.

The cephalometrics films are generally taken by setting the standard of the head with a rod called Ear-rod applied to the right and left external auditory meatuses. However, they vary to some extent in the setting and are limited in accuracy. Further, they are radiographs for making the human body transparent. In the case of a lateral cephalogram, for example, right and left bones are overlapped with each other, so that a measuring area may, in some cases, be difficult to see.

In recent years, an image processing technique (computer software) capable of constructing tomographing data obtained by a tomograph called CT (Computed Tomography) or MRI (Magnetic Resonance Imaging) in three dimensions on a computer and observing a skull has been developed.

In the existing computer software, it is possible to construct a three-dimensional image (3D image) on a display on the basis of the multi-tomographing image data, freely rotate and move the 3D image on the display, and observe the 3D image at an arbitrary viewpoint.

It is also possible to arbitrarily set a portion (a range) to be cut, the position thereof, and the direction of the cutting on the display, and display an image on a cut plane.

In the current computer system and software, however, it is impossible to perform processing for setting reference planes using landmarks as a basis, displaying a three-dimensional image based on the set reference planes, and rotating the three-dimensional image on the basis of the set reference planes.

When an attempt to compare past data and current data relating to one patient is made, therefore, images to be displayed are not respectively images using anatomic landmarks as a basis but images displayed using reference axes which have been positioned at the time of radiographing as a basis. Moreover, the reference axes which have been positioned at the time of radiographing are set every time the radiographing is performed. Therefore, the two images to be compared do not conform to each other in the reference axes, so that both the images cannot be correctly compared with each other.

Similarly, even when the skeletal forms, for example, of a plurality of patients are compared with one another, each of the images is constructed as a three-dimensional image on the basis of the reference axes which have been positioned at the time of radiographing. Accordingly, a plurality of images cannot be compared with one another on the basis of the same reference axes.

DISCLOSURE OF INVENTION

The present invention has been made under such a background and has for its object to provide a display device capable of displaying a three-dimensional image on a display on the basis of multi-tomographing data, specifying a plurality of anatomic landmarks appearing on the displayed image, to create reference planes using the specified landmarks as a basis, and correcting the displayed image to an image based on the reference planes which have been created using the landmarks as a basis, a display processing method, and an image displaying program therefor.

The invention as set forth in claim 1 is directed to a device for displaying a three dimensional image, characterized by comprising tomographing data storage means storing multi-tomographing image data; display means; three-dimensional image construction means for constructing a three-dimensional image on the basis of the multi-tomographing image data stored in the tomographing data storage means and displaying the constructed three-dimensional image on the display means; coordinate storing means for storing coordinates of a predetermined number of anatomic landmarks which are specified in the three-dimensional image displayed on the display means; reference plane creation means for creating anatomic reference planes on the basis of the stored coordinates of the landmarks; and three-dimensional image correction means for correcting the three-dimensional image constructed by the three-dimensional image construction means to a three-dimensional image whose position representation has been corrected on the basis of the created anatomic reference planes.

The invention as set forth in claim 2 is the device for displaying a three-dimensional image as set forth in claim 1, characterized in that the three-dimensional image correction means displays the corrected three-dimensional image on the display means.

The invention as set forth in claim 3 is the device for displaying a three-dimensional image as set forth in claim 2, characterized in that the anatomic reference planes created by the reference plane creation means are displayed together with the corrected three-dimensional image on the display means.

The invention as set forth in claim 4 is the display device according to any one of claims 1 to 3, characterized by further comprising: display control means for displaying on the display means a two-dimensional image based on the anatomic reference planes in response to a requirement that a tomographing image or a cut plane should be displayed with respect to the three-dimensional image whose position representation has been corrected on the basis of the created anatomic reference planes.

The invention as set forth in claim 5 is the device for displaying a three-dimensional image as set forth in any one of claims 1 to 4, characterized in that the anatomic reference planes include a horizontal reference plane which is a plane for separating upper and lower parts of the head, a coronal plane which is a plane for separating front and rear parts thereof, and a median plane which is a plane for separating right and left parts thereof.

The invention as set forth in claim 6 is directed to a method of displaying a three-dimensional image, characterized by comprising the steps of creating a tomographing data file storing multi-tomographing image data; constructing a three-dimensional image on the basis of the multi-tomographing image data stored in the file and displaying the constructed three-dimensional image on a display; displaying, when an anatomic landmark in the displayed three-dimensional image is specified, the landmark on the three-dimensional image as well as storing the coordinates of the landmark; taking, in response to specification of at least three landmarks, a plane passing through the coordinates of the three landmarks as a first reference plane; taking a plane passing through a line segment connecting the two landmarks out of the three landmarks and perpendicular to the first reference plane as a second reference plane; taking a plane passing through the remaining one landmark other than the two landmarks out of the three landmarks and respectively perpendicular to the first reference plane and the second reference plane as a third reference plane; and correcting and displaying the coordinates of the three-dimensional image such that an Xo-axis, a Yo-axis, a Zo-axis respectively forming the first reference plane, the second reference plane, and the third reference plane are used as a basis.

The invention as set forth in claim 7 is directed to a method of displaying a three-dimensional image, characterized by comprising the steps of creating a tomographing data file storing multi-tomographing image data; constructing a three-dimensional image on the basis of the multi-tomographing image data stored in the file and displaying the constructed three-dimensional image on a display; displaying, when an anatomic landmark in the displayed three-dimensional image is specified, the landmark on the three-dimensional image as well as storing the coordinates of the landmark; taking, in response to specification of at least three landmarks, a plane passing through the coordinates of the three landmarks as a first reference plane; taking, in response to further specification of two landmarks (which can be overlapped with the landmarks previously specified), a plane passing through a line segment connecting the two landmarks and perpendicular to the first reference plane as a second reference plane; taking, in response to further specification of one landmark (which can be overlapped with the landmarks previously specified), a plane passing through the landmark and respectively perpendicular to the first reference plane and the second reference plane as a third reference plane; and correcting and displaying the coordinates of the three-dimensional image such that an Xo-axis, a Yo-axis, a Zo-axis respectively forming the first reference plane, the second reference plane, and the third reference plane are used as a basis.

The invention as set forth in claim 8 is the method of displaying a three-dimensional image as set forth in claim 6 or 7, wherein the first reference plane, the second reference plane and the third reference plane and/or the Xo-axis, the Yo-axis and the Zo-axis can be together displayed on the three-dimensional image which is corrected and displayed.

The invention as set forth in claim 9 is the display method according to any one of claims 6 to 8, characterized in that a two-dimensional image based on the reference planes is displayed in response to a requirement that a certain tomographing image or a certain cut plane of the three-dimentional image should be displayed.

The invention as set forth in claim 10 is the method of displaying a three-dimensional image as set forth in any one of claims 6 to 9, characterized in that the first reference plane is a horizontal reference plane for separating upper and lower parts of the head, the second reference plane is a coronal plane for separating front and rear parts thereof, and the third reference plane is a median plane for separating right and left parts thereof.

The invention as set forth in claim 11 is directed to a computer readable recording medium having a program recorded thereon, the program causing a computer to execute processing for forming in a memory area a tomographing data file storing multi-tomographing image data comprising a lot of layers; processing for forming in a memory area a three-dimensional image data file represented by an XYZ coordinate system; processing for address-converting the multi-tomographing image data into three-dimensional data on the three-dimensional image data file, positioning the three-dimensional data on the three-dimensional image data file, and displaying a three-dimensional image; processing for creating, in response to specification of at least three anatomic landmarks in the displayed three-dimensional image, planes including the three landmarks as anatomic reference planes; and processing for correcting the address of the three-dimensional data on the basis of the created anatomic reference planes.

The invention as set forth in claim 12 is the computer readable recording medium as set forth in claim 11, characterized in that the processing for creating the anatomic reference planes comprises processing for taking, in response to specification of at least three anatomic landmarks in the displayed three-dimensional image, a plane passing through the coordinates of the three landmarks as a first reference plane; processing for taking, in response to further specification of two landmarks (which may be overlapped with the landmarks previously specified), a plane passing through a line segment connecting the two landmarks and perpendicular to the first reference plane as a second reference plane; and processing for taking, in response to further specification of one landmark (which may be over lapped with the landmarks previously specified), a plane passing through the landmark and respectively perpendicular to the first reference plane and the second reference plane as a third reference plane.

The invention as set forth in claim 13 is the computer readable recording medium as set forth in claim 12, comprising processing for displaying the three-dimensional data whose address has been corrected.

The invention as set forth in claim 14 is the computer readable recording medium according to claim 13, comprising processing for displaying, as a two-dimensional data based on the three-dimensional data whose address has been corrected and displayed, the two-dimensional image displayed in response to the requirement for displaying a tomographing image or a cut plane of an arbitrarily portion of the displayed three-dimensional image.

The invention as set forth in claim 15 is the computer readable recording medium as set forth in claim 13, comprising processing for displaying the anatomic reference planes (the first reference plane, the second reference plane, and the third reference plane), together with the three-dimensional data whose address has been corrected.

The invention as set forth in claim 16 is a program for a computer, comprising: processing for forming a tomographing data file storing multi-tomographing image data comprising a lot of layers, processing for forming a three-dimensional image data file represented by an XYZ coordinate system; processing for address-converting the multi-tomographing image data into three-dimensional data on the three-dimensional image data file, positioning the three-dimensional data on the three-dimensional image data file, and displaying a three-dimensional image; processing for creating, in response to specification of at least three anatomic landmarks in the displayed three-dimensional image, planes including the three landmarks as anatomic reference planes; and processing for correcting the address of the three-dimensional data on the basis of the created anatomic reference planes.

The invention as set forth in claim 17 is the program according to claim 16, characterized in that the processing for creating the anatomic reference planes comprises processing for taking, in response to specification of at least three anatomic landmarks in the displayed three-dimensional image, a plane passing through the coordinates of the three landmarks as a first reference plane; processing for taking, in response to further specification of two landmarks (which may be overlapped with the landmarks previously specified), a plane passing through a line segment connecting the two landmarks and perpendicular to the first reference plane as a second reference plane; and processing for taking, in response to further specification of one landmark (which may be overlapped with the landmarks previously specified), a plane passing through the landmark and respectively perpendicular to the first reference plane and the second reference plane as a third reference plane.

The invention as set forth in claim 18 is the program according to claim 17, comprising processing for displaying the three-dimensional data whose address has been corrected.

The invention as set forth in claim 19 is the program according to claim 18, comprising processing for displaying the anatomic reference planes (the first reference plane, the second reference plane, and the third reference plane), together with the three-dimensional data whose address has been corrected.

According to the present invention, in a medical computer system, the display position (the coordinate value or the address) of a three-dimensional image displayed on a display can be corrected to that of a three-dimensional image using anatomic reference planes as a basis. Consequently, the image to be displayed in three dimensions is not an image displayed on the basis of reference axes at the time of radiographing but an image based on the anatomic reference planes. Accordingly, the three-dimensional image can be anatomically directed. On anatomy, it is possible to measure, evaluate, and compare the forms of images from a correct direction on morphology or a direction in which reproducibility is always obtained.

Furthermore, the three-dimensional image displayed on the basis of the reference planes can be also, of course, rotated at an arbitrary angle and cut in an arbitrary cross section, as in the conventional example. Also in the case, the anatomic reference planes are used as a basis. Accordingly, it is possible to obtain a three-dimensional image having reproducibility and a tomogram on a cut surface.

MODES FOR CARRYING OUT THE INVENTION

Figure 1A:
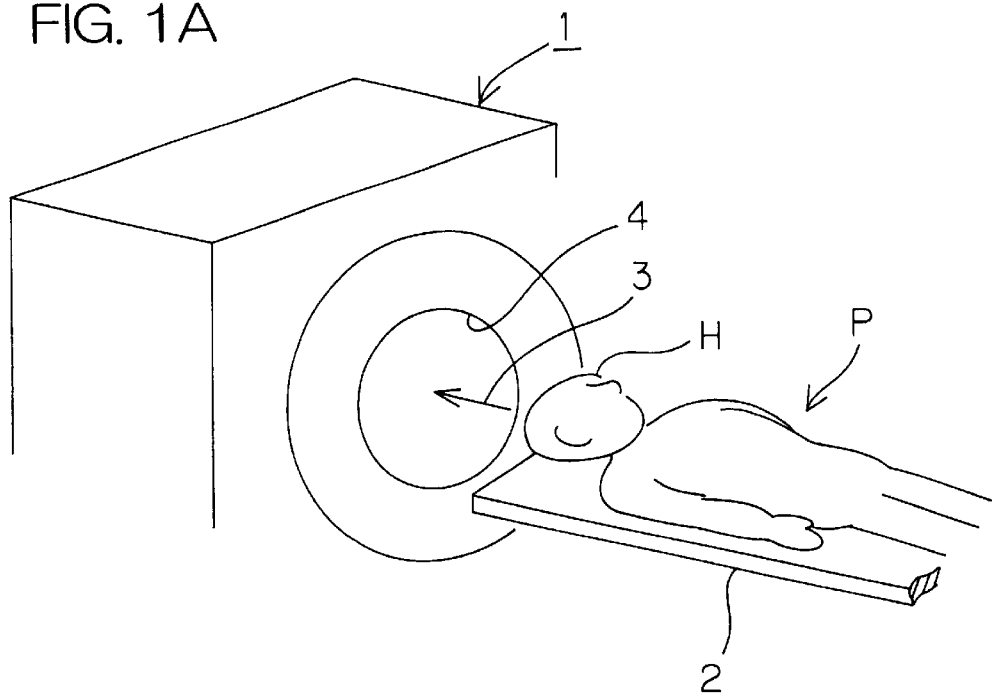
FIG. 1A is an illustration showing how a patient is tomographed by a CT device.

Referring now to the drawings, an embodiment of the present invention will be specifically described.

Problems to be solved by the invention will be specifically described once again.

FIG. 1A is an illustration showing how the head H or the like of a patient P is tomographed using a CT device 1. The patient P lies face up at a predetermined position on a stand 2. At this time, the body of the patient P is fixed by a simple engaging device or the like, if required. The stand 2 moves in a direction indicated by an arrow 3, and enters a ring 4. The tomographing is performed by an image pick-up portion spirally moving along a peripheral surface of the ring 4. Consequently, multi-tomographing data is obtained.

Figure 1B:
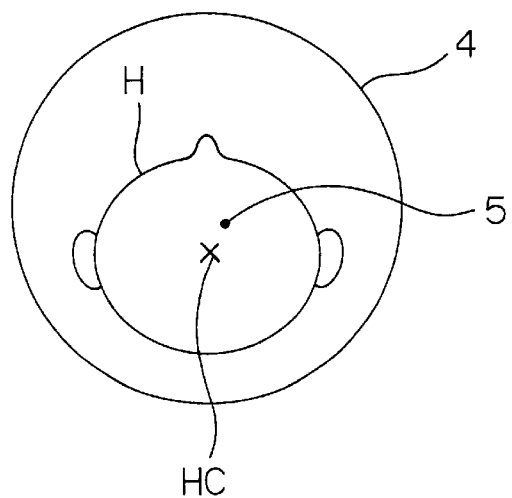
FIG. 1B is an illustration for explaining that the central axis of a CT device's ring and the central axis of the head of the patient do not necessarily coincide with each other.

However, as shown in FIG. 1B, the central axis 5 of the ring 4 and the central axis of the head H of the patient who has entered the ring 4 do not necessarily coincide with each other. In many cases, the two axes are rather shifted from each other. Further, the central axis of the head H of the patient and the central axis 5 of the ring 4 differ in the amount of shift and the direction of shift every time the tomographing is performed.

Therefore, tomographing data obtained by the CT device 1 becomes tomographing data relating to the head H of the patient, as viewed from the ring 4, and is data using the position for tomographing (the position of the ring 4) as a basis.

Figure 2:
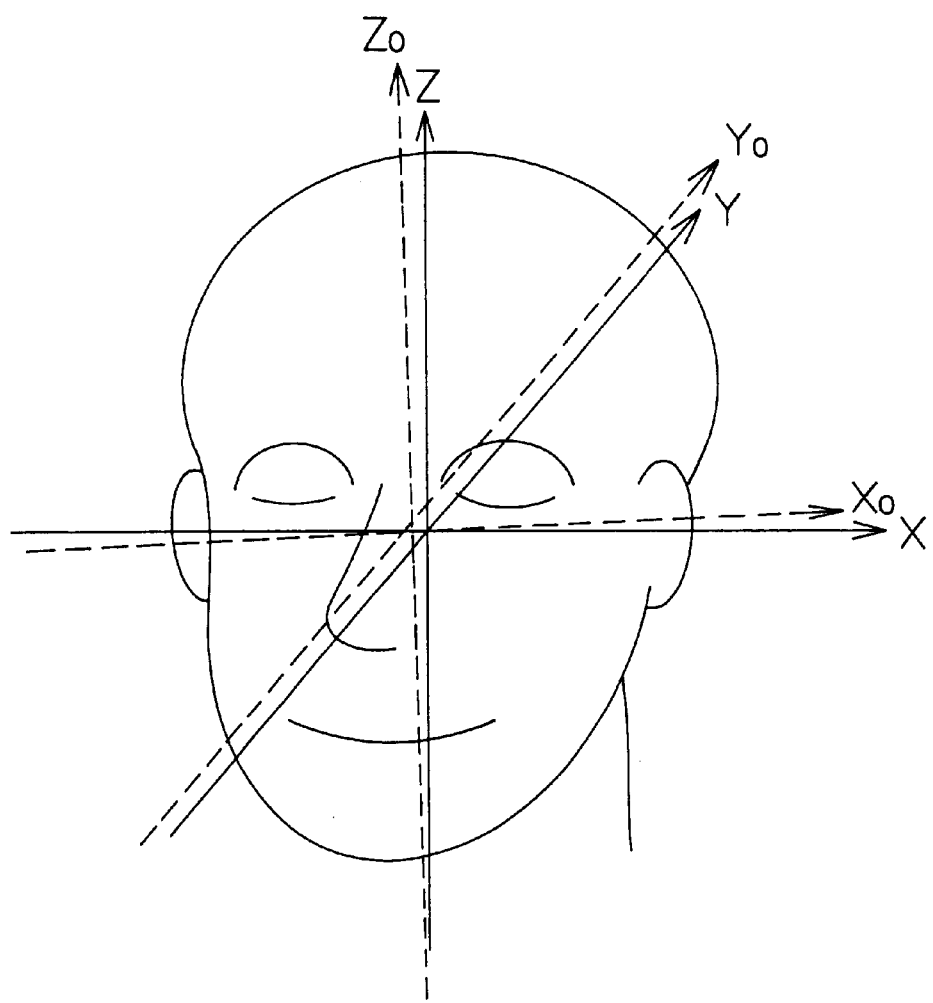
FIG. 2 is a diagram showing reference axes X, Y, and Z at the time of radiographing in a three-dimensional image and reference axes Xo, Yo, and Zo based on anatomic landmarks.

When multi-tomographing image data obtained from the CT device is constructed as a three-dimensional image, therefore, its reference axes X, Y, and Z are determined on the basis of the reference position at the time of radiographing (the position of the ring 4), as shown in FIG. 2.

On the other hand, in order to correctly grasp the skeletal form, the position of the teeth, and so forth, of the patient, a three-dimensional image using reference axes Xo, Yo, and Zo set on the basis of predetermined anatomic landmarks as a basis must be observed.

However, the conventional three-dimensional image is an image based on the reference axes X, Y, and Z at the time of radiographing, as described above, so that the reference axes differ for each image. Even if images are compared with each other, and the right and left positions, the inclination, and so forth of the same image are measured, therefore, there are some problems. For example, accurate values cannot be obtained.

In the present embodiment, there are provided a computer system capable of converting the three-dimensional image based on the reference axes X, Y, and Z at the time of radiographing into the image based on the reference three planes based on the anatomic landmarks, to display the three-dimensional image using the reference planes by the landmarks as a basis and a method of displaying such an image.

Figure 3:
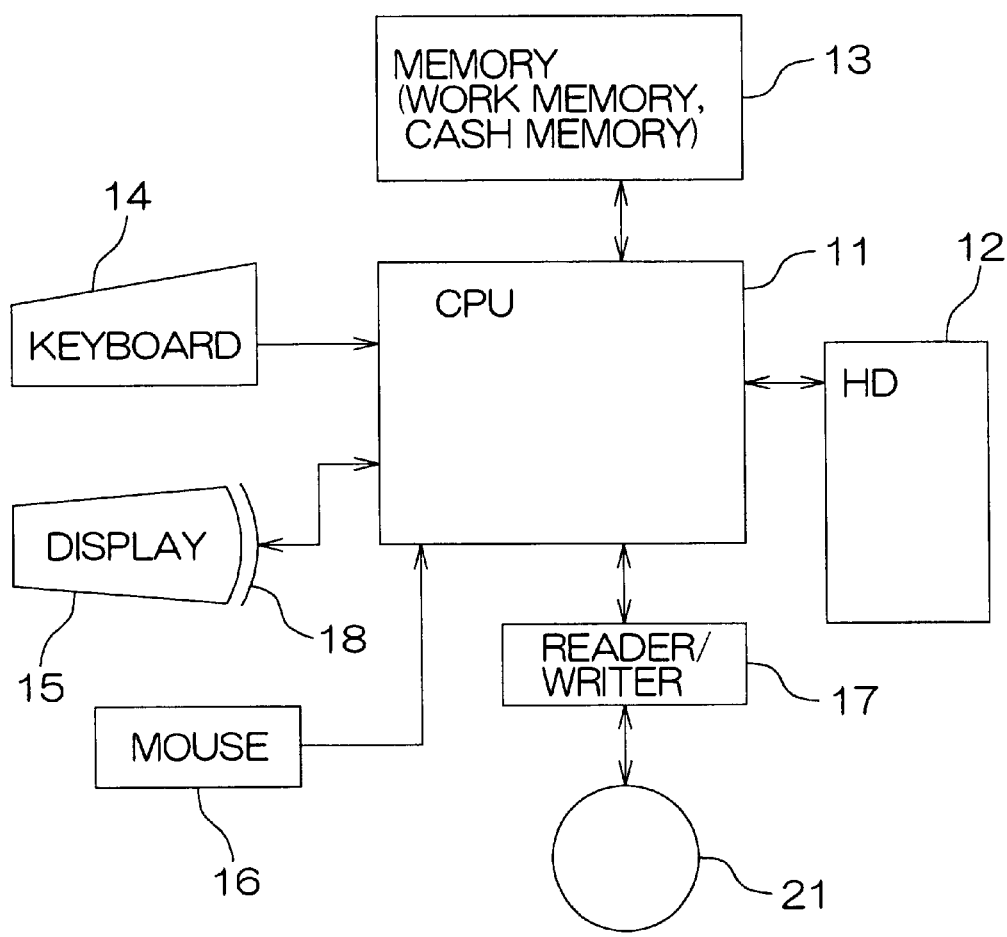
FIG. 3 is a block diagram showing the configuration of a computer system according to an embodiment of the present invention.

FIG. 3 is a block diagram showing the configuration of a computer system according to an embodiment of the present invention. The system comprises a CPU 11 serving as a processing center. A hard disk 12 serving as a large-capacity memory and a memory 13 such as a work memory such as a RAM or a cash memory are connected to the CPU 11. A memory other than the foregoing memories may be, of course, connected to the CPU 11.

Furthermore, a keyboard 14 for entering data and a command, a display 15 for displaying data, an image, and so forth, a mouse 16, and a reader/writer 17 for reading data recorded on a recording medium 21 and writing the data into the recording medium 21 are respectively connected to the CPU 11. The display 15 may comprise a so-called touch panel structure 18 on its display surface. A specified place on the display surface may be set, and a command key or the like appearing on the display surface may be able to be pressed.

Figure 4:
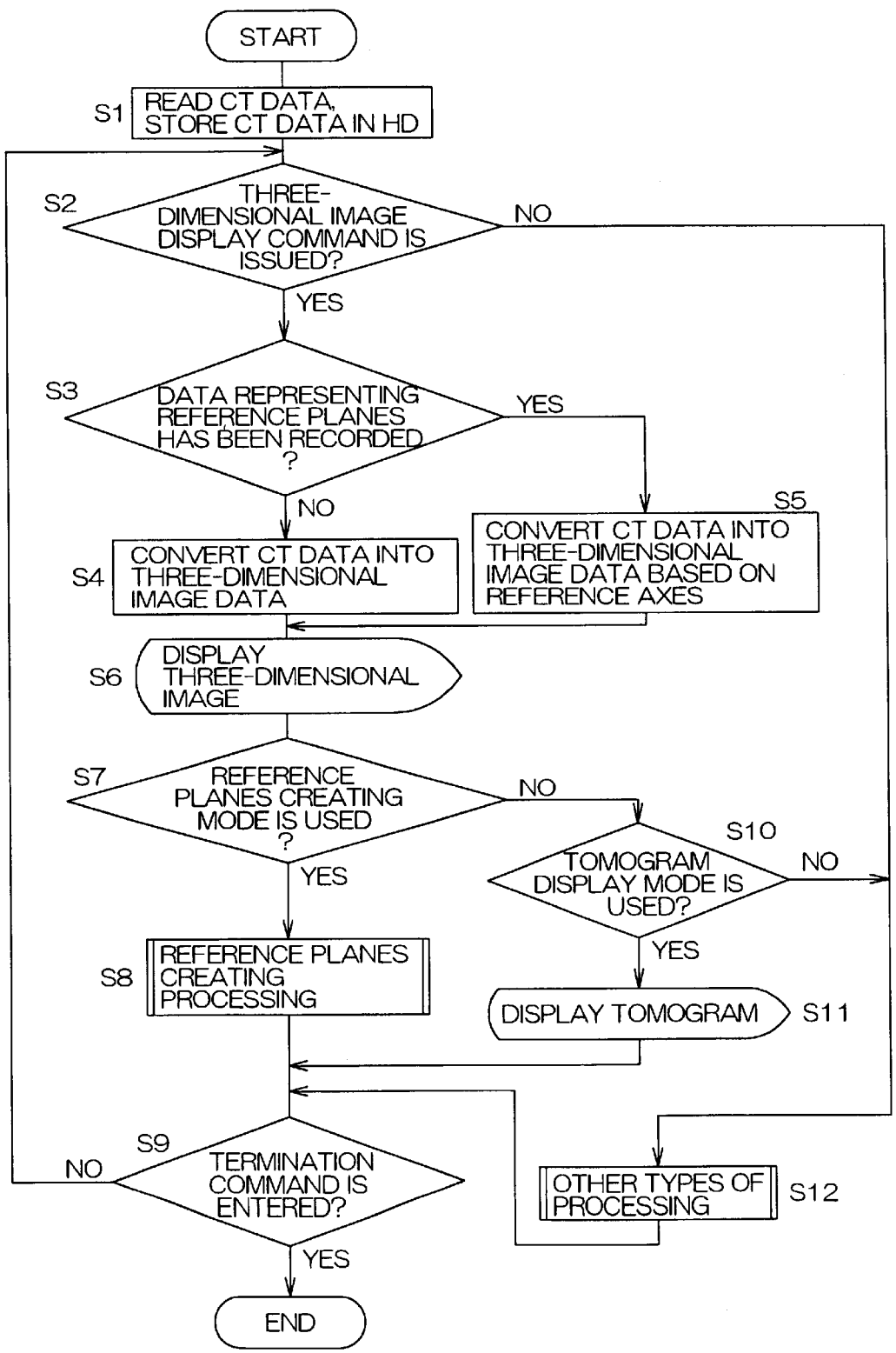
FIG. 4 is a flow chart showing the outline of the whole of a processing operation executed by the system shown in FIG. 3.

FIG. 4 is a flow chart showing the outline of the overall processing operation executed by the system shown in FIG. 3. In accordance with the flow of FIG. 4, the outline of the entire contents of processing executed by the system shown in FIG. 3 will be first described.

Multi-tomographing image data obtained by radiographing using the CT device (hereinafter referred to as CT data) is recorded on the information recording medium 21 such as an optical disk, a flexible disk, or a DVD (Digital Video Disk). The information recording medium 21 is set in the reader/writer 17. A reading start switch, for example, is pressed, so that the CT data recorded on the information recording medium 21 is read and is recorded on the hard disk 12, so that a tomographing data file is created (step S1).

After the reading of the CT data is completed, when a three-dimensional image display command is issued upon operation of the keyboard 14 or the mouse 16 (step S2), the CPU 11 judges whether or not data representing reference planes by landmarks has already been recorded on the hard disk 12 or the memory 13 (step S3).

In an initial state, the data representing reference planes by landmarks is not recorded. Accordingly, processing for converting the CT data which is recorded as the tomographing data file on the hard disk 12 into three-dimensional image data on the basis of reference axes at the time of radiographing is performed (step S4). A three-dimensional image data file is created in the cash memory 13 by the conversion.

The three-dimensional image data obtained by the conversion is fed to the display 15, so that a three-dimensional image is displayed on the display 15 (step S6).

When the data representing reference planes by landmarks exists (YES at step S3), the CT data which has been read out of the hard disk 12 is not merely converted into three-dimensional image data but converted into three-dimensional image data and positionaly corrected based on reference planes by landmarks (step S5) and then, the image data is displayed as a three-dimensional image (step S6).

Figure 5:
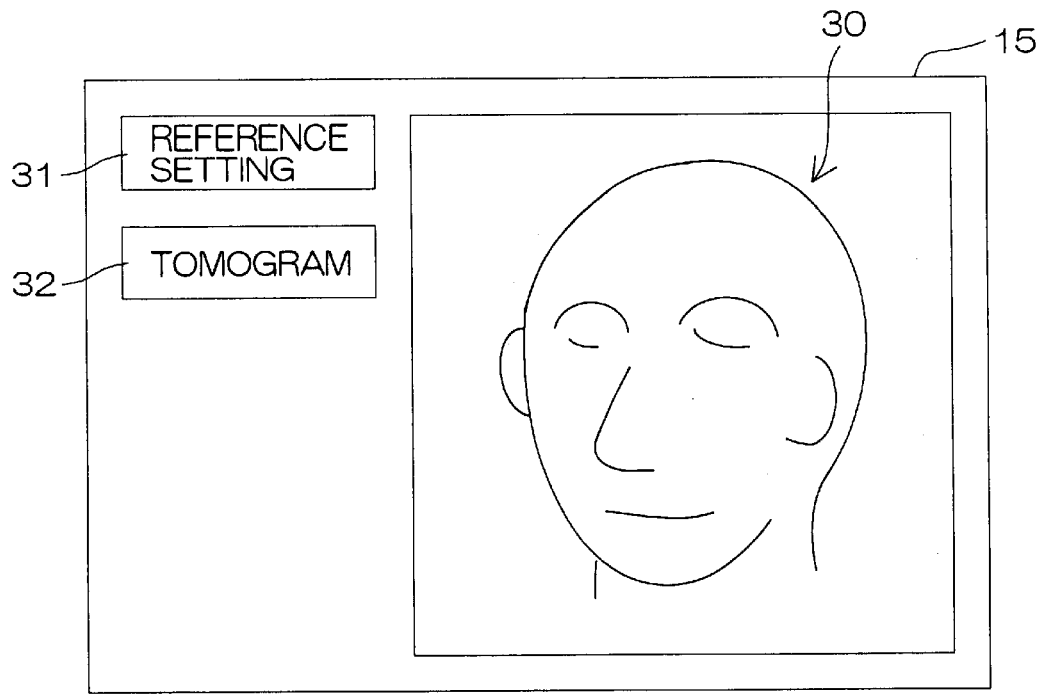
FIG. 5 is a diagram showing an example of display on a display 15.

The CPU 11 then judges whether or not a mode for creating reference planes by landmarks is used (step S7). For example, a key 31 for setting the mode for creating reference planes, together with a three-dimensional image 30, is displayed, as shown in FIG. 5, on the display 15. A cursor is moved to the key 31 by the mouse, and the mouse is clicked, for example, so that processing by the CPU 11 proceeds to processing for creating reference planes by landmarks (step S8). The details of the processing for creating reference planes by landmarks will be described later.

Figure 6:
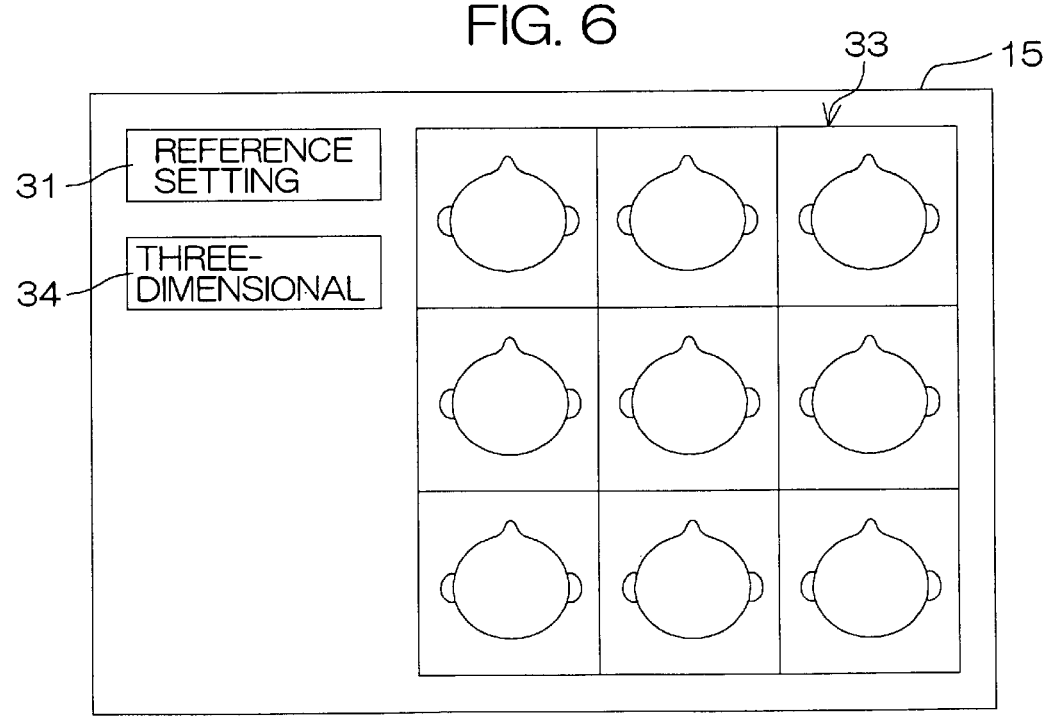
FIG. 6 is a diagram showing an example of display on the display 15.

When it is judged at the step S7 that the mode for creating reference planes by landmarks is not used, the CPU 11 judges whether or not a tomogram display mode is used (step S10). For example, a three-dimensional image 30 as well as a key 32 for setting the tomogram display mode are displayed, as shown in FIG. 5, on the display 15. The key is specified by the cursor, and the mouse is clicked, for example, so that a tomogram is displayed in place of the three-dimensional image which has been displayed on the display 15 (step 11). A plurality of (for example, 9 or 16) tomograms 33 may be simultaneously displayed, as illustrated in FIG. 6. One of the tomograms can be also displayed in enlarged fashion by moving the cursor to the tomogram by the mouse and clicking the mouse.

Furthermore, when the three-dimensional image display command is not entered at the step S2, or it is not judged at the step S10 that the tomogram display mode is used, the program proceeds to other types of processing which are not related to the features of the present invention (step S12).

A termination command is entered (step 9), so that the processing is terminated.

In steps S10 and S11, the tomogram being displayed is a tomogram based on the reference plane based on the anatomic landmarks or a tomogram based on the reference axes at the time of radiographing. In a case where the process goes through with YES in step S3, three-dimensional data converted in step S5 based on the reference plane is displayed in step S6. In this step, the tomogram being displayed is also based on the reference plane.

More specifically, by setting the reference plane based on the anatomic landmarks, the three-dimensional image is displayed on the basis of the set reference plane, and further, the tomogram or the cut plane of the three-dimensional image is displayed as the two-dimensional image also based on the reference plane.

Accordingly, when the reference plane based on the anatomic landmarks has been set, the set reference plane is also used as a basis for displaying the two-dimensional image. In other words, the two-dimensional image is displayed by using the same basis that used for displaying the three-dimensional image. Therefore, in displaying the two-dimensional image, it is possible to obtain an image having good reproducibility, as well as accurate analysis on measurement.

The processing for creating reference planes by landmarks, described at the step S8, will be specifically described. The processing is one of the features of the present embodiment.

Figure 7:
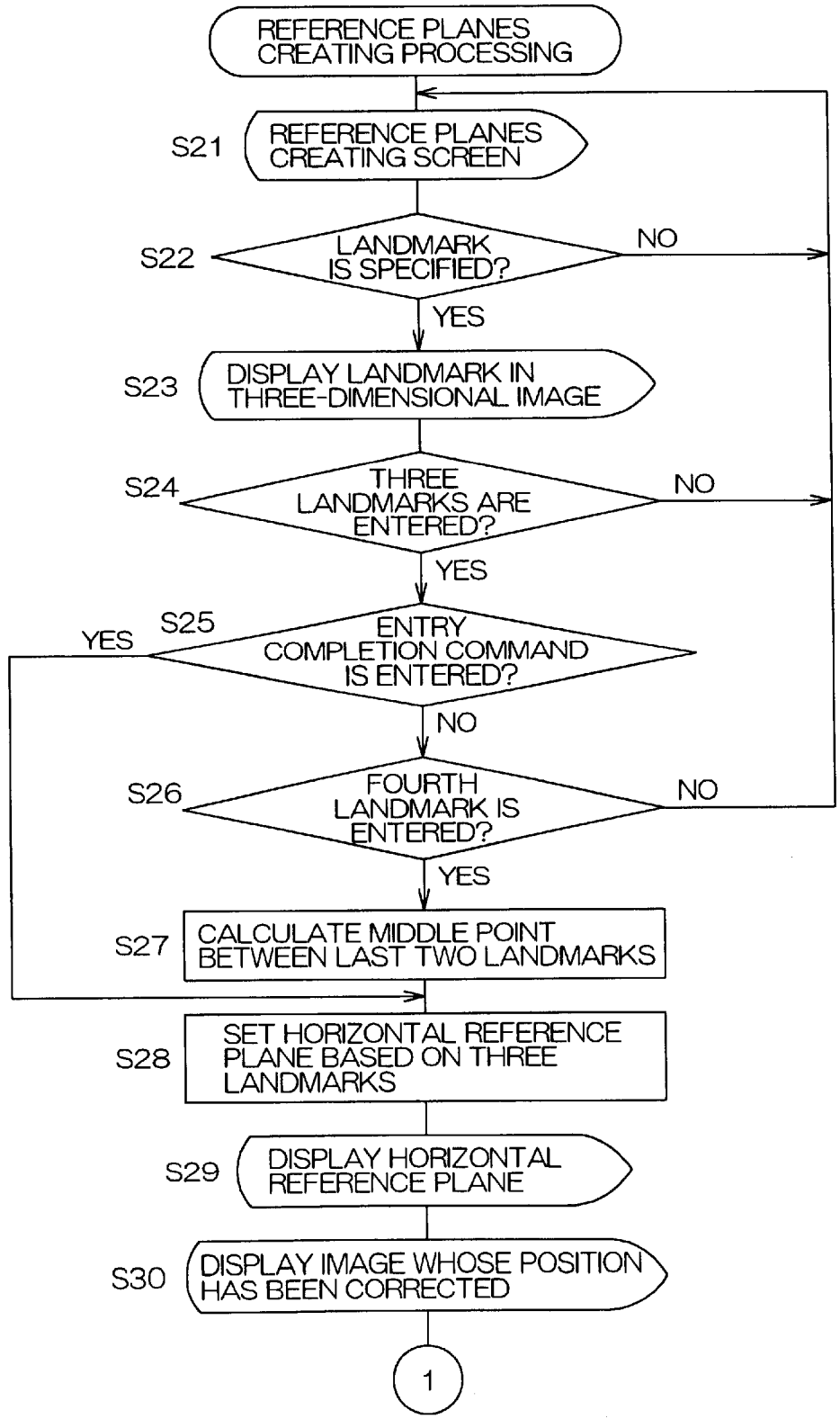
FIG. 7 is a flow chart showing processing for creating reference planes based on the anatomic landmarks.
Figure 8:
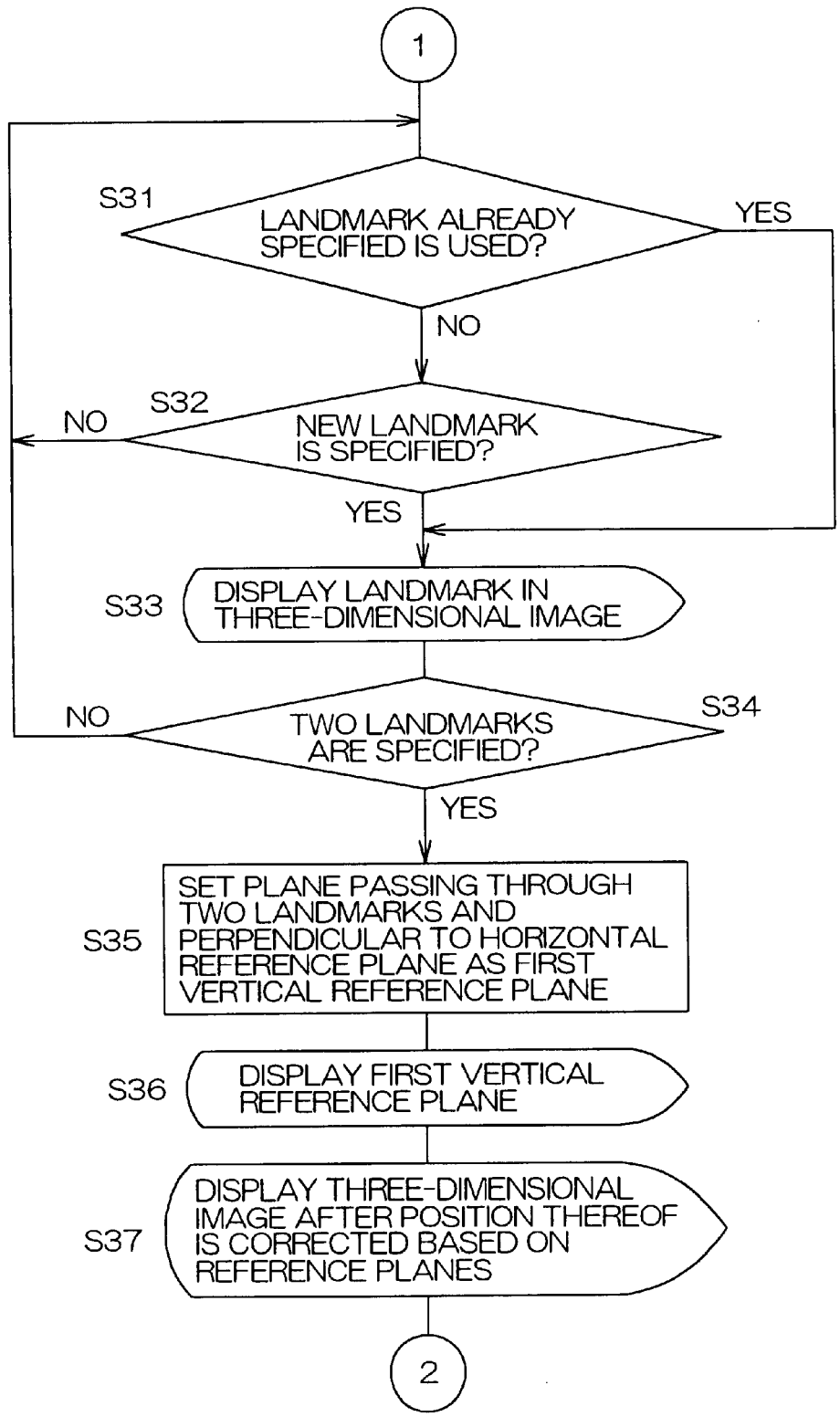
FIG. 8 is a flow chart showing processing for creating reference planes based on the anatomic landmarks.
Figure 9:
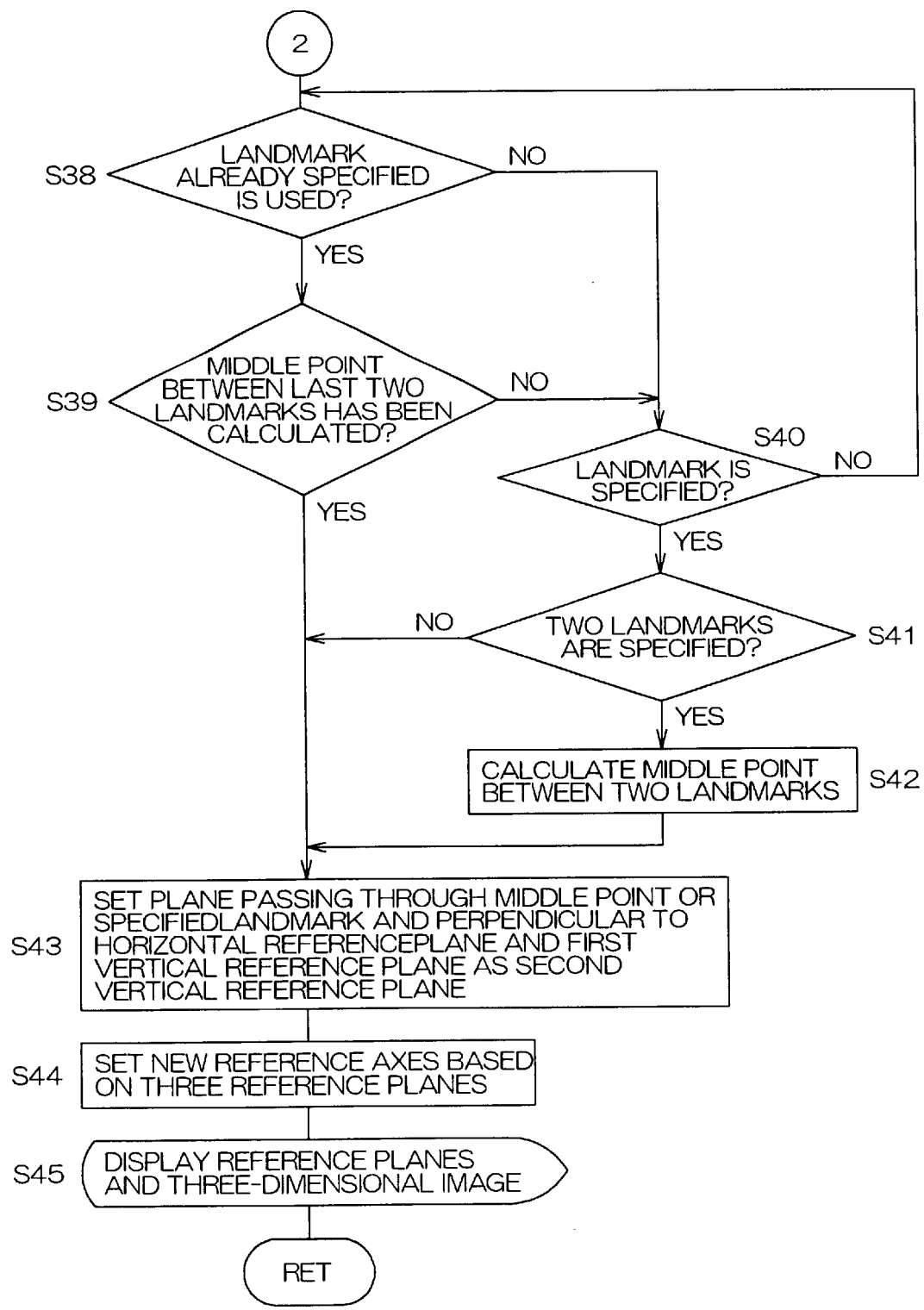
FIG. 9 is a flow chart showing processing for creating reference planes based on the anatomic landmarks.

FIGS. 7 through 9 are flow charts showing the processing for creating reference planes by landmarks.

Figure 10:
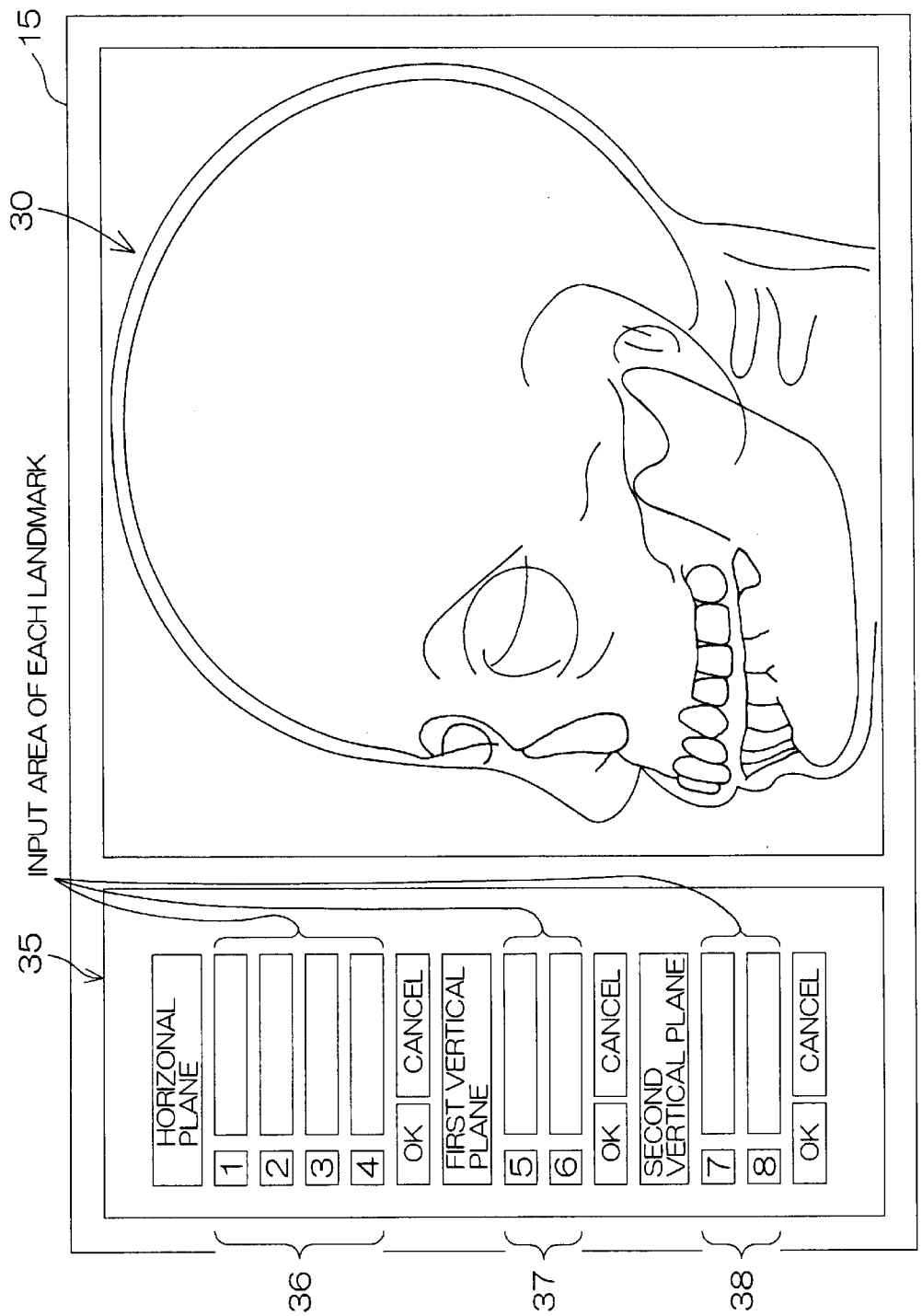
FIG. 10 is a diagram showing an example of display on the display 15.

In this processing, a three-dimensional image 30 of the patient is first displayed on the display 15, and a reference plane creating screen 35 is displayed, as shown in FIG. 10 (step S21).

An area 36 where landmark numbers 1 to 4 for entering a horizontal reference plane is displayed, an area 37 where landmark numbers 5 and 6 for entering a first vertical reference plane is displayed, and an area 38 where landmark numbers 7 and 8 for specifying a second vertical reference plane is displayed are displayed on the reference plane creating screen 35. Specifying the reference plane generally begins by specifying the horizontal reference plane. A button assigned any one of the landmark numbers 1 to 4 to be specified is pressed, and the landmark corresponding to the button is specified on the three-dimensional image 30, so that the landmark is determined in correspondence with the specified landmark number. A mark is displayed on a place (the landmark) specified on the three-dimensional image 30. Further, the name of the landmark (for example, "a left porion") can be also entered in correspondence with the landmark number.

In the specifying landmarks, the landmark previously specified can be also reused as the landmark later specified.

In FIG. 10, a skeleton image whose surface layer, corresponding to the skin of the head H of the patient, has been made transparent is displayed as the three-dimensional image 30. In the processing for creating reference planes, anatomic landmarks on bones are points in determining reference planes. Accordingly, an image of a skeletal form is displayed as a three-dimensional image. When the three-dimensional image is constructed on the basis of the CT data, it is possible to determine which of an image of the appearance (the skin), a skeleton image whose surface layer is made transparent, and an image of the internal form of the skeleton image is used as the three-dimensional image by changing the degree of transparency and the display level.

The three-dimensional skeleton image 30 can be rotated and moved rightward and leftward, upward and downward, and obliquely. A user specifies a necessary landmark on the three-dimensional image while displaying the three-dimensional skeleton image 30 by changing a viewpoint.

When the landmark is specified (step S22), the specified landmark is displayed in the three-dimensional image 30 (step S23).

Description is made by taking as an example a case where a Frankfort Horizontal (FH plane) which is one of typical horizontal reference planes is set on the image. The Frankfort Horizontal is a horizontal plane including right and left porions and middle point between right and left orbitales or either one of orbitales.

Figure 11:
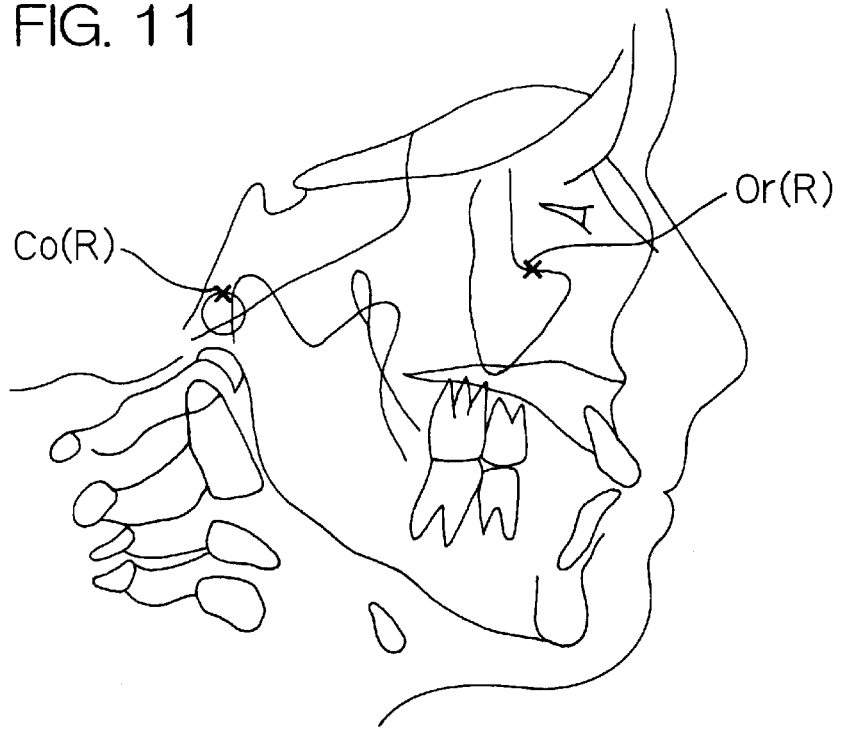
FIG. 11 is a diagram for explaining how a right porion and a right orbitale are specified.

In order to set the horizontal plane, the three-dimensional skeleton image 30 as shown in FIG. 10 is rotated, to specify a right porion Po(R) and a right orbitale Or(R) at an angle at which it is the easiest to confirm, for example, an angle shown in FIG. 11.

Figure 12:
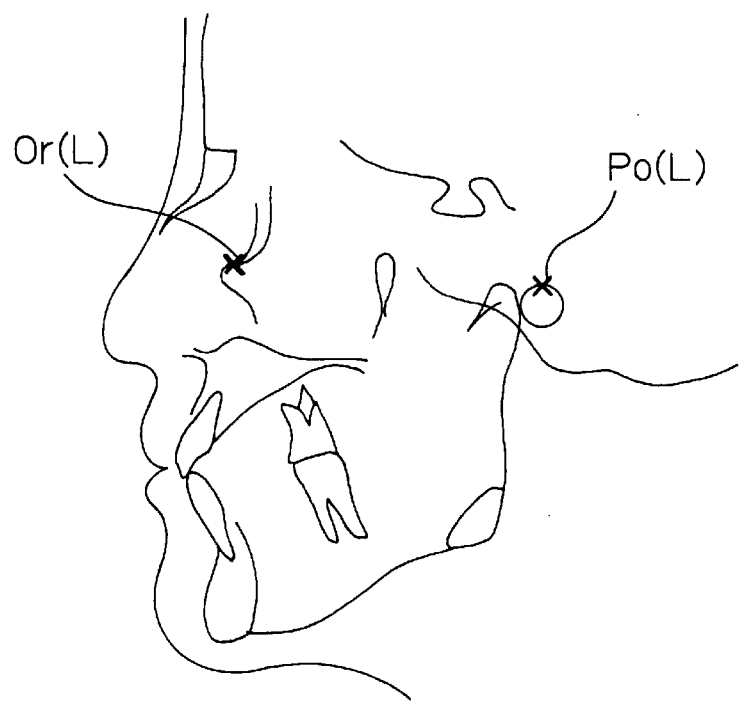
FIG. 12 is a diagram for explaining how a left porion and a left orbitale are specified.

Similarly, a left image as shown in FIG. 12 is displayed, to specify a left porion Po(L) and a left orbitale Or(L).

In the CPU 11, when it is judged that the four landmarks 1 to 4 are entered (step S26), a middle point between the landmarks 3 and 4 which have been entered in correspondence with the landmark numbers 3 and 4 is calculated (step S27).

A horizontal reference plane is set on the basis of the entered two landmarks 1 and 2 and the landmark at the calculated middle point (step S28).

In the entry of the landmarks at the steps S22-26, the landmarks are specified while seeing the three-dimensional skeleton image at an arbitrary viewpoint, so that the landmarks can be correctly entered.

In the above-mentioned example, a middle point between right and left orbitales is taken as a landmark of an orbital, so that the right and left orbitales are entered as landmarks. However, either one of the orbitales may be entered as a landmark. In the case, if one of the orbitales is entered as a landmark (step S24), and an entry completion command is then entered, a horizontal reference plane is set at the step S28.

The set horizontal reference plane is displayed upon being overlapped with the three-dimensional skeleton image (step S29). If a horizontal reference plane (a Frankfort Horizontal) is set, the position representation of the image is corrected on the basis of the set horizontal reference plane (step S30).

In order to then determine where is the front of the image which has been able to be horizontally positioned, a mode for entering a first vertical reference plane creating screen is used.

In the processing, a landmark which has already been specified can be used. In a case where the landmark is used, when the landmark number thereof is entered, the landmark is displayed in a three-dimensional image (step S33). Specifically, right and left porions which have been previously specified can be used as two landmarks for setting a first vertical reference plane.

When the landmark which has been previously specified is not used, a new landmark may be, of course, specified on the three-dimensional image (step S32), and the specified landmark is displayed in the three-dimensional image (step s33).

When the CPU 11 judges that two landmarks have been specified and determined (step S34), a plane passing through the two landmarks and perpendicular to the horizontal reference plane which has been previously determined is set as a first vertical reference plane (step S35).

Figure 13:
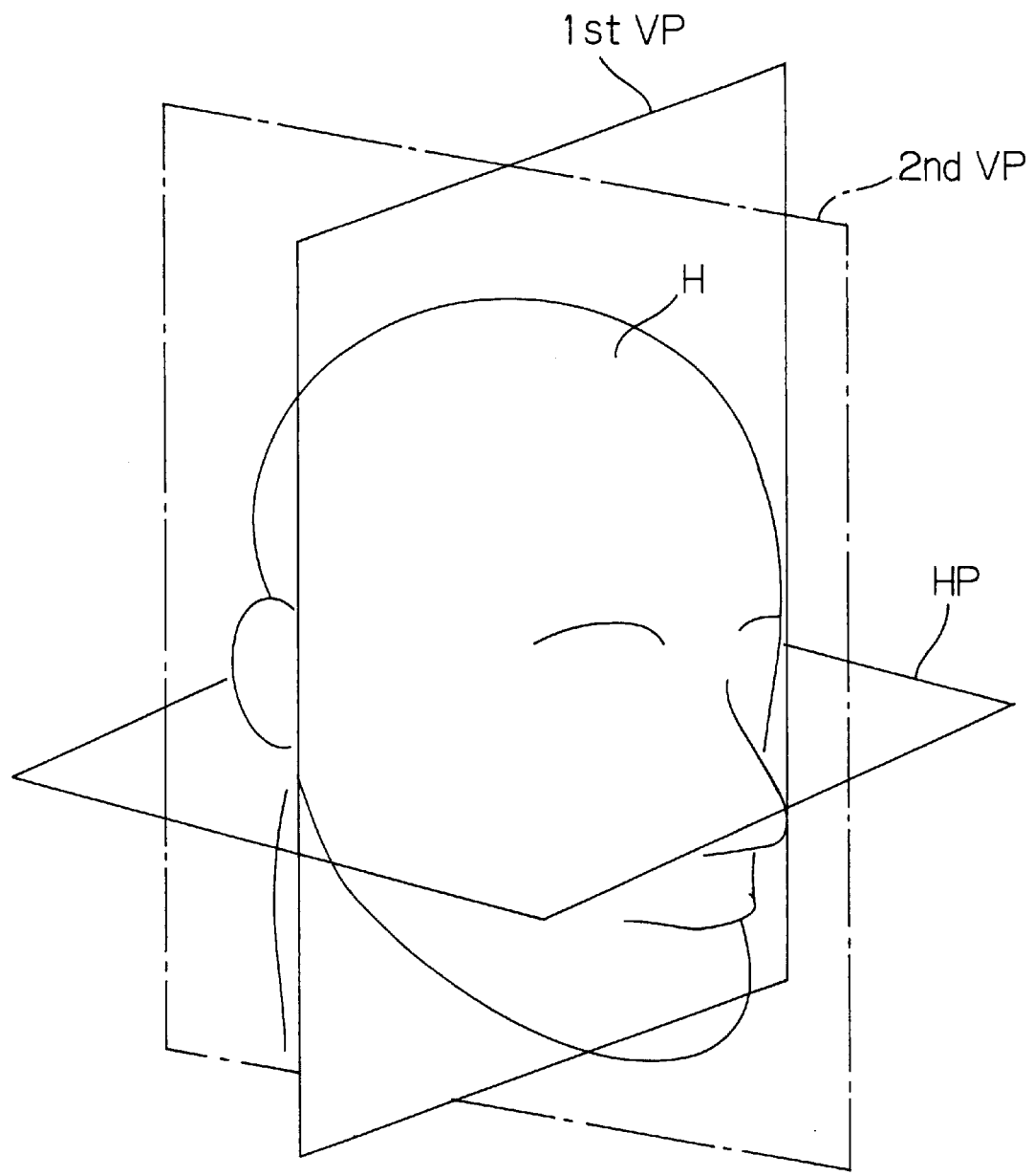
FIG. 13 is a diagram showing a three-dimensional image of the head H, a horizontal reference plane, a first vertical reference plane, and a second vertical reference plane.

The first vertical reference plane is called as a coronal plane which is indicated as 1stVP in FIG. 13. The head H is divided into front and rear parts by the first vertical reference plane 1stVP.

As shown in FIG. 13, the position representation of a three-dimensional image is corrected on the basis of the set horizontal reference plane and first vertical reference plane, and the three-dimensional image is displayed together with the reference planes (steps S36 and S37).

A second vertical reference plane (a median plane) for dividing the head into right and left parts is then set. The second vertical reference plane is a plane perpendicular to the horizontal reference plane and the first vertical reference plane. Accordingly, the second vertical reference plane can be determined if only one landmark is specified or two landmarks are specified to specify a middle point therebetween.

Even in setting the second vertical reference plane, a landmark which has already been specified can be used. When the landmark is used, it is judged whether or not the landmark is calculated as a middle point between right and left orbitales (step S39).

If the landmark which has already been specified is not used, a new landmark can be also specified (step S40). Only one landmark may be specified. Accordingly, it is possible to choose whether only one landmark is specified or a middle point between two landmarks is found (steps S41 and S42).

When one landmark or a middle point between two landmarks is finally calculated, a plane passing through the specified one landmark or the calculated middle point between the two landmarks and perpendicular to the horizontal reference plane and the first vertical reference plane is set as a second vertical reference plane (step S43).

New reference axes, that is, an $X_0$-axis, a $Y_0$-axis, and a $Z_0$-axis are determined on the basis of the set three reference planes (step S44).

The set reference planes and new reference axes are displayed, and a three-dimensional image whose position representation has been corrected by the reference planes is displayed (step S45).

In a case where a three-dimensional image being displayed is based on the reference plane based on the anatomic landmarks, a tomogram or a cut plane thereof, that is, a two-dimensional image is also based on the reference plane. Therefore, similarly to the three-dimensional image, when a tomogram or a cut plane is created using an arbitrarily portion of the three-dimensional image on the basis of the reference plane, the tomogram or the cut plane (two-dimensional image) to be created has good reproducibility by using the same reference plane as a basis.

In the above-mentioned embodiment, when the horizontal reference plane, the first vertical reference plane, and the second vertical reference plane are set, the set reference planes are successively displayed upon being overlapped with the three-dimensional skeleton image, and the position representation of the image is also corrected. However, the overlapping display of the reference planes and the correction of the position representation of the image may be collectively performed in the end.

The anatomic reference planes (the first reference plane, the second reference plane, and the third reference plane) need not be necessarily displayed together with the three-dimensional image. The anatomic reference planes may be able to be displayed on the screen by an user's operation, only when required.

As described in the foregoing, the anatomic reference planes by the landmarks are set, so that the three-dimensional image is displayed upon changing the position thereof on the basis of the reference planes. The three-dimensional image which is display ed as if it were floating in the space without having any basis can be anatomically directed. Therefore, on anatomy, it is possible to measure, evaluate, and compare the forms of images from a correct direction on morphology or a direction in which reproducibility is always obtained.

Furthermore, the anatomic reference planes are set, and the position of the three-dimensional image is corrected on the basis of the reference planes. Therefore, it is possible to repeatedly use conditions for setting a cut surface based on the anatomic reference planes, for example, the degree at which the three-dimensional image is inclined from the reference plane and millimeters by which the three-dimensional image is positioned above, below, behind or ahead of the reference plane. Accordingly, the same area can be repeatedly observed in the same direction and at the same position. That is, even if the reference axes at the time of radiographing are changed every time the radiographing is performed, the positions of the landmarks on the bones of the patient and the reference planes based on the landmarks are not changed. Consequently, it is possible to compare a plurality of data in the same patient and compare the data between the patient and another patient or cases with reproducibility.

More specifically, it is possible to measure the shortest distance from an arbitrary point to the anatomic reference plane and an angle formed between an arbitrary straight line and the anatomic reference plane. Further, it is possible to diagnose and evaluate the positional relationship between arbitrary areas on the basis of the anatomic reference planes. Therefore, images obtained from examining devices such as CT, MRI, SPECT (Single Photon Emission Computed Tomography), or a plurality of images of the same patient are overlapped with one another by the anatomic reference planes, thereby making it possible to compare, diagnose, and evaluate both the images.

Furthermore, by coloring the whole or a part, for example, of the image based on the anatomic reference planes and overlapping the image with an image of gnathoplasy or the like, it is possible to visually display the simulation of the gnathoplasy.

Furthermore, even if the time when the image is positioned is not the time of radiographing, the positioning can be corrected on a computer. Accordingly, a radiographer need not be so nervous of positioning the patient at the time of radiographing. Accordingly, secondary effects are produced. For example, it is possible to significantly shorten time and labor for radiographing.

The present invention is not limited to the above-mentioned embodiment, and various changes can be made within the range of the claims.

This application claims priority benefits under the Treaty on the basis of Japanese Patent Applications Nos. 11-185865 and 2000-153563 filed to the Japanese Patent Office on Jun. 30, 1999 and May 24, 2000, respectively, the disclosure thereof being incorporated herein by reference.

What is claimed is:

1. A device for displaying a three dimensional image, by comprising tomographing data storage means storing multi-tomographing image data;

display means;

three-dimensional image construction means for constructing a three-dimensional image on the basis of the multi-tomographing image data stored in the tomographing data storage means and displaying the constructed three-dimensional image on said display means;

coordinate storing means for storing coordinates of at least three anatomic landmarks which are specified in the three-dimensional image displayed on the display means;

reference plane creation means for creating anatomic reference planes on the basis of the stored coordinates of the at least three landmarks, wherein the reference plane creation means takes a plane passing through the coordinates of the specified landmarks as a first reference plane, a plane passing through a line segment connecting two of the specified landmarks, which may be overlapped with the landmarks previously used for reference plane creation, and perpendicular to the first reference plane as a second reference plane, and a plane passing through one of the specified landmarks, which may be overlapped with the landmarks previously used for reference plane creation, and perpendicular to the first reference plane and the second reference plane as a third reference plane; and three-dimensional image correction means for correcting the three-dimensional image constructed by the three-dimensional image construction means to a three-dimensional image whose position representation has been corrected on the basis of the created anatomic reference planes.

2. The display device according to claim 1, wherein said three-dimensional image correction means displays the corrected three-dimensional image on said display means.

3. The display device according to claim 2, wherein the anatomic reference planes created by said reference plane creation means are displayed together with the corrected three-dimensional image on said display means.

4. The display device according to claim 1, characterized by further comprising:
  display control means for displaying on the display means a two-dimensional image based on the anatomic reference planes in response to a requirement that a tomographing image or a cut plane should be displayed with respect to the three-dimensional image whose position representation has been corrected on the basis of the created anatomic reference planes.

5. The display device according to claim 1, wherein the anatomic reference planes include a horizontal reference plane which is a plane for separating upper and lower parts of the head, a coronal plane which is a plane for separating front and rear parts thereof, and a median plane which is a plane for separating right and left parts thereof.

6. A method of displaying a three-dimensional image, comprising the steps of:
  creating a tomographing data file storing multi-tomographing image data;
  constructing a three-dimensional image on the basis of the multi-tomographing image data stored in the file and displaying the constructed three-dimensional image on a display;
  displaying, when an anatomic landmark in the displayed three-dimensional image is specified, the landmark on the three-dimensional image as well as storing the coordinates of the landmark;
  taking, in response to specification of at least three landmarks, a plane passing through the coordinates of the specified landmarks as a first reference plane;
  taking, in response to further specification of two landmarks, which may overlapped with the landmarks previously specified, a plane passing through a line segment connecting the two further specified landmarks and perpendicular to the first reference plane as a second reference plane;
  taking, in response to yet further specification of one landmark, which may be overlapped with the landmarks previously specified, a plane passing through the yet further specified landmark and respectively perpendicular to the first reference plane and the second reference plane as a third reference plane; and
  correcting and displaying the coordinates of the three-dimensional image such that an Xo-axis, a Yo-axis, a Zo-axis formed at the intersection the first reference plane, the second reference plane, and the third reference plane are used as reference axes.

7. The display method according to claim 6, wherein the first reference plane, the second reference plane and the third reference plane and/or the Xo-axis, the Yo-axis and the Zo-axis can be together displayed on the three-dimensional image which is corrected and displayed.

8. The display method according to claim 6, that wherein a two-dimensional image based on the reference planes is displayed in response to a requirement that a certain tomographing image or a certain cut plane of the three-dimensional image should be displayed.

9. The display method according to claim 6, wherein the first reference plane is a horizontal reference plane for separating upper and lower parts of the head, the second reference plane is a coronal plane for separating front and rear parts thereof, and the third reference plane is a median plane for separating right and left parts thereof.

10. A computer readable recording medium having a program recorded thereon, the program causing a computer to execute:
  processing for forming in a memory area a tomographing data file storing multi-tomographing image data comprising a plurality of layers,
  processing for forming in the memory area a three-dimensional image data file represented by an XYZ coordinate system;
  processing for address-converting the multi-tomographing image data into three-dimensional data on the three-dimensional image data file, positioning the three-dimensional data on the three-dimensional image data file, and displaying a three-dimensional image;
  processing for creating, in response to specification of at least three anatomic landmarks in the displayed three-dimensional image, planes including the at least three landmarks as anatomic reference planes;
  wherein said processing for creating the anatomic reference planes comprises:
  processing for taking, in response to specification of the at least three anatomic landmarks in the displayed three-dimensional image, a plane passing through the coordinates of the specified landmarks as a first reference plane;
  processing for taking, in response to further specification of two landmarks, which may be overlapped with the landmarks previously specified, a plane passing through a line segment connecting the two further specified landmarks and perpendicular to the first reference plane as a second reference plane; and
  processing for taking, in response to yet further specification of one landmark, which may be overlapped with the landmarks previously specified, a plane passing through the yet further specified landmark and respectively perpendicular to the first reference plane and the second reference plane as a third reference plane; and
  processing for correcting the address of the three-dimensional data on the basis of the created anatomic reference planes.

11. The computer readable recording medium according to claim 10, wherein the recorded program further causes the computer to execute:

processing for displaying the three-dimensional data whose address has been corrected.

12. The computer readable recording medium according to claim 11, wherein the recorded program further causes the computer to execute:

processing for displaying, as a two-dimensional data based on the three-dimensional data whose address has been corrected and displayed, the two-dimensional image displayed in response to the requirement for displaying a tomographing image or a cut plane of an arbitrarily portion of the displayed three-dimensional image.

13. The computer readable recording medium according to claim 11, wherein the recorded program further causes the computer to execute:

processing for displaying the anatomic reference planes, including first reference plane, the second reference plane, and the third reference plane, together with the three-dimensional data whose address has been corrected.

14. A program for a computer, comprising:

processing for forming a tomographing data file storing multi-tomographing image data comprising a lot of layers, processing for forming a three-dimensional image data file represented by an XYZ coordinate system;

processing for address-converting the multi-tomographing image data into three-dimensional data on the three-dimensional image data file, positioning the three-dimensional data on the three-dimensional image data file, and displaying a three-dimensional image;

processing for creating, in response to specification of at least three anatomic landmarks in the displayed three-dimensional image, planes including the three landmarks as anatomic reference planes;

wherein the processing for creating the anatomic reference planes comprises:

processing for taking, in response to specification of at least three anatomic landmarks in the displayed three-dimensional image, a plane passing through the coordinates of the specified landmarks as a first reference plane;

processing for taking, in response to further specification of two landmarks, which may be overlapped with the landmarks previously specified, a plane passing through a line segment connecting the two further specified landmarks and perpendicular to the first reference plane as a second reference plane; and processing for taking, in response to yet further specification of one landmark, which may be overlapped with the landmarks previously specified, a plane passing through the yet further specified landmark and respectively perpendicular to the first reference plane and the second reference plane as a third reference plane; and processing for correcting the address of the three-dimensional data on the basis of the created anatomic reference planes.

15. The program according to claim 14, further comprising:

processing for displaying the three-dimensional data whose address has been corrected.

16. The program according to claim 15, further comprising:

processing for displaying the anatomic reference planes, including first reference plane, the second reference plane, and the third reference plane, together with the three-dimensional data whose address has been corrected.

* * * * *